United States Patent
Alfaro et al.

(10) Patent No.: US 7,662,185 B2
(45) Date of Patent: Feb. 16, 2010

(54) INTERVERTEBRAL IMPLANTS

(75) Inventors: Arthur A. Alfaro, Colts Neck, NJ (US); Lawrence A. Shimp, Morganville, NJ (US); James L. Russell, Little Silver, NJ (US); John W. Boyle, Upper Montclair, NJ (US); Erik O. Martz, Howell, NJ (US); Daniel E. Rosenthal, Millburn, NJ (US); John W. Morris, Beachwood, NJ (US)

(73) Assignee: Osteotech, Inc., Eatontown, NJ (US)

( * ) Notice: Subject to any disclaimer, the term of this patent is extended or adjusted under 35 U.S.C. 154(b) by 672 days.

(21) Appl. No.: 10/651,390

(22) Filed: Aug. 28, 2003

(65) Prior Publication Data
US 2004/0044409 A1 Mar. 4, 2004

Related U.S. Application Data

(62) Division of application No. 09/754,038, filed on Jan. 2, 2001, now abandoned.

(60) Provisional application No. 60/173,973, filed on Dec. 30, 1999.

(51) Int. Cl.
*A61F 2/44* (2006.01)
(52) U.S. Cl. .................. 623/17.16; 623/17.11
(58) Field of Classification Search ............... 623/17.11, 623/17.16
See application file for complete search history.

(56) References Cited

U.S. PATENT DOCUMENTS

| 1,025,008 | A | 4/1912 | Miner |
| 2,375,116 | A | 5/1945 | Larkin |
| 2,525,222 | A | 10/1950 | Holt |
| 3,068,916 | A | 12/1962 | Richardson |
| 3,486,505 | A | 12/1969 | Morrison |
| 3,604,298 | A | 9/1971 | Dekiel |
| 3,604,487 | A | 9/1971 | Gilbert |

(Continued)

FOREIGN PATENT DOCUMENTS

AU 744371 11/1998

(Continued)

OTHER PUBLICATIONS

International Search Report of PCT/US01/00112 mailed Apr. 18, 2001.

(Continued)

*Primary Examiner*—David Isabella
*Assistant Examiner*—Yashita Sharma
(74) *Attorney, Agent, or Firm*—Kenneth E. Levitt; Dorsey & Whitney LLP

(57) ABSTRACT

A multipart intervertebral implant is provided which includes an implant portion and an implant extender portion. The implant portion and the implant extender portion can be fastened together using any known fastening means including pins, interlocking structure (e.g., dovetail, tongue and groove, etc.), adhesives, etc. The size of the implant extender portion can be selected during a surgical procedure to provide an implant suitable for a particular intervertebral receiving bed. An intervertebral implant is also provided which may be formed from a multiplicity of implant sections which are fastened together to provide an implant having a desired length. Implants having surface configurations which more closely correspond to the configuration of vertebral endplates are also provided.

13 Claims, 13 Drawing Sheets

U.S. PATENT DOCUMENTS

| | | |
|---|---|---|
| 3,703,006 A | 11/1972 | Bokros et al. |
| 3,848,601 A | 11/1974 | Ma et al. |
| 4,033,244 A | 7/1977 | Jacobson |
| 4,059,115 A | 11/1977 | Jumashev et al. |
| 4,185,383 A | 1/1980 | Heimke et al. |
| 4,273,117 A | 6/1981 | Neuhauser |
| 4,349,921 A | 9/1982 | Kuntz |
| 4,394,370 A | 7/1983 | Jefferies |
| 4,416,278 A | 11/1983 | Miller |
| 4,440,750 A | 4/1984 | Glowacki et al. |
| 4,484,570 A | 11/1984 | Sutter et al. |
| 4,485,097 A | 11/1984 | Bell |
| 4,516,276 A | 5/1985 | Mittelmeier et al. |
| 4,553,575 A | 11/1985 | Brown |
| 4,559,936 A | 12/1985 | Hill |
| 4,566,466 A | 1/1986 | Ripple et al. |
| 4,573,448 A | 3/1986 | Kambin |
| 4,637,931 A | 1/1987 | Schmitz |
| 4,649,918 A | 3/1987 | Pegg et al. |
| 4,678,470 A | 7/1987 | Nashef et al. |
| 4,714,469 A | 12/1987 | Kenna |
| 4,743,256 A | 5/1988 | Brantigan |
| 4,743,259 A | 5/1988 | Bolander et al. |
| 4,753,235 A | 6/1988 | Hasson |
| 4,772,287 A | 9/1988 | Ray et al. |
| 4,782,833 A | 11/1988 | Einhorn |
| 4,798,213 A | 1/1989 | Doppelt |
| 4,820,305 A | 4/1989 | Harms et al. |
| 4,834,757 A | 5/1989 | Brantigan |
| 4,863,477 A | 9/1989 | Monson |
| 4,877,020 A | 10/1989 | Vich |
| 4,878,915 A | 11/1989 | Brantigan |
| 4,904,261 A | 2/1990 | Dove et al. |
| 4,917,704 A | 4/1990 | Frey et al. |
| 4,932,973 A | 6/1990 | Gendler |
| 4,938,768 A | 7/1990 | Wu |
| 4,950,296 A | 8/1990 | McIntyre |
| 4,955,885 A | 9/1990 | Meyers |
| 4,961,740 A | 10/1990 | Ray et al. |
| 4,963,154 A * | 10/1990 | Anapliotis et al. ....... 623/22.28 |
| 4,997,434 A | 3/1991 | Seedhom et al. |
| 5,015,247 A | 5/1991 | Michelson |
| 5,015,255 A | 5/1991 | Kuslich |
| 5,026,373 A | 6/1991 | Ray et al. |
| 5,047,058 A | 9/1991 | Roberts et al. |
| 5,049,150 A | 9/1991 | Cozad |
| 5,053,049 A | 10/1991 | Campbell |
| 5,055,104 A | 10/1991 | Ray |
| 5,061,786 A | 10/1991 | Burnier et al. |
| 5,062,845 A | 11/1991 | Kuslich et al. |
| 5,112,354 A | 5/1992 | Sires |
| 5,171,278 A | 12/1992 | Pisharodi |
| 5,192,321 A | 3/1993 | Strokon |
| 5,192,327 A | 3/1993 | Brantigan |
| 5,197,967 A | 3/1993 | Wilson |
| 5,207,710 A | 5/1993 | Chu et al. |
| 5,236,456 A | 8/1993 | O'Leary et al. |
| 5,284,655 A | 2/1994 | Bogdansky et al. |
| 5,298,254 A | 3/1994 | Prewett et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,312,408 A | 5/1994 | Brown |
| 5,314,476 A | 5/1994 | Prewett et al. |
| 5,314,478 A | 5/1994 | Oka et al. |
| 5,361,483 A | 11/1994 | Rainville et al. |
| 5,380,333 A | 1/1995 | Meloul et al. |
| 5,390,683 A | 2/1995 | Pisharodi |
| 5,397,364 A | 3/1995 | Kozak et al. |
| 5,423,817 A | 6/1995 | Lin |
| 5,423,825 A | 6/1995 | Levine |
| 5,425,772 A | 6/1995 | Brantigan |
| 5,425,773 A | 6/1995 | Boyd et al. |
| 5,439,684 A | 8/1995 | Prewett et al. |
| 5,443,514 A | 8/1995 | Steffee |
| 5,445,639 A | 8/1995 | Kuslich et al. |
| 5,458,638 A | 10/1995 | Kuslich et al. |
| 5,458,643 A | 10/1995 | Oka et al. |
| 5,484,437 A | 1/1996 | Michelson |
| 5,489,307 A | 2/1996 | Kuslich et al. |
| 5,489,308 A | 2/1996 | Kuslich et al. |
| 5,490,962 A | 2/1996 | Cima et al. |
| 5,505,731 A | 4/1996 | Tornier |
| 5,505,732 A | 4/1996 | Michelson |
| 5,507,813 A | 4/1996 | Dowd et al. |
| 5,514,180 A | 5/1996 | Heggeness et al. |
| 5,518,680 A | 5/1996 | Cima et al. |
| 5,522,899 A | 6/1996 | Michelson |
| 5,534,028 A | 7/1996 | Bao et al. |
| 5,534,030 A | 7/1996 | Navarro et al. |
| 5,545,222 A | 8/1996 | Bonutti |
| 5,554,191 A | 9/1996 | Lahille et al. |
| 5,562,738 A | 10/1996 | Boyd et al. |
| 5,571,190 A | 11/1996 | Ulrich et al. |
| 5,571,192 A | 11/1996 | Schonhoffer |
| 5,591,235 A | 1/1997 | Kuslich |
| 5,593,409 A | 1/1997 | Michelson |
| 5,607,269 A | 3/1997 | Dowd et al. |
| 5,607,424 A | 3/1997 | Tropiano |
| 5,609,635 A | 3/1997 | Michelson |
| 5,609,636 A | 3/1997 | Kohrs et al. |
| 5,632,747 A | 5/1997 | Scarborough et al. |
| 5,645,596 A | 7/1997 | Kim et al. |
| 5,645,598 A | 7/1997 | Brosnahan, III |
| 5,653,761 A | 8/1997 | Pisharodi |
| 5,653,762 A | 8/1997 | Pisharodi et al. |
| 5,653,763 A | 8/1997 | Errico et al. |
| 5,658,336 A | 8/1997 | Pisharodi |
| 5,658,337 A | 8/1997 | Kohrs et al. |
| 5,662,710 A | 9/1997 | Bonutti |
| 5,669,909 A | 9/1997 | Zdeblick et al. |
| 5,683,394 A | 11/1997 | Rinner |
| 5,683,463 A | 11/1997 | Godefroy et al. |
| 5,683,464 A | 11/1997 | Wagner et al. |
| 5,702,391 A | 12/1997 | Lin |
| 5,707,371 A | 1/1998 | Metz-Stavenhagen |
| 5,709,683 A | 1/1998 | Bagby |
| 5,716,415 A | 2/1998 | Steffee |
| 5,716,416 A | 2/1998 | Lin |
| 5,720,751 A | 2/1998 | Jackson |
| 5,728,159 A | 3/1998 | Stroever et al. |
| 5,741,253 A | 4/1998 | Michelson |
| 5,749,916 A | 5/1998 | Richelsoph |
| 5,766,251 A | 6/1998 | Koshino |
| 5,766,252 A | 6/1998 | Henry et al. |
| 5,769,897 A | 6/1998 | Harle |
| 5,776,199 A | 7/1998 | Michelson |
| 5,782,830 A | 7/1998 | Farris |
| 5,782,919 A | 7/1998 | Zdeblick et al. |
| 5,785,710 A | 7/1998 | Michelson |
| 5,800,547 A | 9/1998 | Schafer et al. |
| 5,807,437 A | 9/1998 | Sachs et al. |
| 5,814,084 A | 9/1998 | Grivas et al. |
| 5,824,078 A | 10/1998 | Nelson et al. |
| 5,824,094 A | 10/1998 | Serhan et al. |
| 5,846,484 A | 12/1998 | Scarborough et al. |
| 5,860,973 A | 1/1999 | Michelson |
| 5,865,845 A | 2/1999 | Thalgott |
| 5,868,749 A | 2/1999 | Reed |
| 5,885,299 A | 3/1999 | Winslow et al. |
| 5,885,300 A | 3/1999 | Tokuhashi et al. |
| 5,888,219 A | 3/1999 | Bonutti |
| 5,888,222 A | 3/1999 | Coates et al. |

| | | | | | | |
|---|---|---|---|---|---|---|
| 5,888,227 | A | 3/1999 | Cottle | 2003/0039676 A1 | 2/2003 | Boyce et al. |
| 5,895,426 | A | 4/1999 | Scarborough et al. | 2003/0049326 A1 | 3/2003 | Nimni |
| 5,895,428 | A | 4/1999 | Berry | 2003/0060825 A1 | 3/2003 | Alfaro et al. |
| 5,899,939 | A | 5/1999 | Boyce et al. | 2003/0130667 A1 | 7/2003 | Lin |
| 5,904,683 | A | 5/1999 | Pohndorf et al. | 2003/0135214 A1 | 7/2003 | Fetto et al. |
| 5,904,719 | A | 5/1999 | Errico et al. | 2003/0147860 A1 | 8/2003 | Marchosky |
| 5,928,238 | A | 7/1999 | Scarborough et al. | 2004/0024457 A1 | 2/2004 | Boyce et al. |
| 5,941,882 | A | 8/1999 | Jammet et al. | 2004/0044409 A1 | 3/2004 | Alfaro et al. |
| 5,968,047 | A | 10/1999 | Reed | 2004/0098129 A1 | 5/2004 | Lin |
| 5,972,368 | A | 10/1999 | McKay | 2004/0146543 A1 | 7/2004 | Shimp et al. |
| 5,980,522 | A | 11/1999 | Koros et al. | 2004/0243242 A1 | 12/2004 | Sybert et al. |
| 5,984,967 | A | 11/1999 | Zdeblick et al. | 2004/0249377 A1 | 12/2004 | Kaes et al. |
| 5,989,289 | A | 11/1999 | Coates et al. | 2005/0008620 A1 | 1/2005 | Shimp et al. |
| 6,025,538 | A | 2/2000 | Yaccarino, III | 2005/0008672 A1 | 1/2005 | Winterbottom et al. |
| 6,030,635 | A | 2/2000 | Gertzman et al. | 2005/0027033 A1 | 2/2005 | Knaack et al. |
| 6,045,554 | A | 4/2000 | Grooms et al. | 2005/0038511 A1 | 2/2005 | Martz et al. |
| 6,045,579 | A | 4/2000 | Hochshuler et al. | 2005/0107880 A1 | 5/2005 | Shimp et al. |
| 6,045,580 | A | 4/2000 | Scarborough et al. | 2005/0143740 A1 | 6/2005 | Morris et al. |
| 6,066,174 | A | 5/2000 | Farris | 2005/0283255 A1 | 12/2005 | Geremakis et al. |
| 6,077,267 | A | 6/2000 | Huene | 2006/0149376 A1 | 7/2006 | Shimp et al. |
| 6,083,225 | A | 7/2000 | Winslow et al. | 2007/0178158 A1 | 8/2007 | Knaack et al. |
| 6,090,143 | A | 7/2000 | Meriwether et al. | | | |
| 6,096,081 | A | 8/2000 | Grivas et al. | | | |

FOREIGN PATENT DOCUMENTS

| | | |
|---|---|---|
| DE | 2 253 086 | 10/1972 |
| DE | 40 12 622 C | 7/1991 |
| DE | 43 02 397 | 7/1993 |
| DE | 198 15 407 | 10/1999 |
| DE | 298 14 174 U | 12/1999 |
| EP | 0 302 719 | 2/1989 |
| EP | 0 307 241 | 3/1989 |
| EP | 0 325 566 | 7/1989 |
| EP | 0 332 826 | 9/1989 |
| EP | 0 493 698 | 7/1992 |
| EP | 0 732 093 | 2/1996 |
| EP | 0 734 703 | 10/1996 |
| EP | 1 064 890 | 1/2001 |
| FR | 2636227 | 3/1990 |
| FR | 2703580 | 10/1994 |
| FR | 2742652 | 6/1997 |
| FR | 2769827 | 4/1999 |
| JP | 01/179689 | 7/1989 |
| SU | 1107854 | 8/1984 |
| SU | 590872 A | 11/1985 |
| WO | WO 89/09035 | 10/1989 |
| WO | WO 93/01771 | 2/1993 |
| WO | WO 94/21298 | 9/1994 |
| WO | WO 97/15246 | 5/1997 |
| WO | WO 97 47258 | 12/1997 |
| WO | WO 98/02117 | 1/1998 |
| WO | WO 98/48738 | 11/1998 |
| WO | WO 99/07312 | 2/1999 |
| WO | WO 99/09914 | 3/1999 |
| WO | WO 99/21515 | 5/1999 |
| WO | WO 99/38461 | 8/1999 |
| WO | WO 00 07527 | 2/2000 |
| WO | WO 00/24327 | 5/2000 |
| WO | WO 00 40177 | 7/2000 |
| WO | WO 00/40179 | 7/2000 |
| WO | WO 01/00792 | 1/2001 |
| WO | WO 01/49220 | 7/2001 |
| WO | WO 01/66048 | 9/2001 |
| WO | WO 01/70136 | 9/2001 |
| WO | WO 01/70137 | 9/2001 |
| WO | WO 01/70139 | 9/2001 |
| WO | WO 01/78798 | 10/2001 |
| WO | WO 03/030956 A2 | 4/2003 |
| WO | WO 2005/072656 | 8/2005 |

| | | | |
|---|---|---|---|
| 6,102,950 | A | 8/2000 | Vaccaro |
| 6,111,164 | A | 8/2000 | Rainey et al. |
| 6,113,637 | A | 9/2000 | Gill et al. |
| 6,113,638 | A | 9/2000 | Williams et al. |
| 6,123,705 | A | 9/2000 | Michelson |
| 6,123,731 | A | 9/2000 | Boyce et al. |
| 6,132,472 | A | 10/2000 | Bonutti |
| 6,136,002 | A | 10/2000 | Shih et al. |
| 6,139,211 | A | 10/2000 | Schroeder et al. |
| 6,143,033 | A | 11/2000 | Paul et al. |
| 6,156,037 | A | 12/2000 | LeHuec et al. |
| 6,159,215 | A | 12/2000 | Urbahns et al. |
| 6,174,311 | B1 | 1/2001 | Branch et al. |
| 6,200,347 | B1 | 3/2001 | Anderson et al. |
| 6,206,923 | B1 | 3/2001 | Boyd et al. |
| 6,210,442 | B1 | 4/2001 | Wing et al. |
| 6,235,059 | B1 | 5/2001 | Benezech et al. |
| 6,258,125 | B1 | 7/2001 | Paul et al. |
| 6,270,528 | B1 | 8/2001 | McKay |
| 6,277,149 | B1 * | 8/2001 | Boyle et al. ............... 623/17.16 |
| 6,294,041 | B1 | 9/2001 | Boyce et al. |
| 6,294,187 | B1 | 9/2001 | Boyce et al. |
| 6,315,795 | B1 | 11/2001 | Scarborough et al. |
| 6,326,018 | B1 | 12/2001 | Gertzman et al. |
| 6,350,283 | B1 | 2/2002 | Michelson |
| 6,379,385 | B1 | 4/2002 | Kalas et al. |
| 6,383,221 | B1 | 5/2002 | Scarborough et al. |
| 6,425,920 | B1 * | 7/2002 | Hamada ................... 623/17.16 |
| 6,432,107 | B1 | 8/2002 | Ferree |
| 6,454,806 | B1 * | 9/2002 | Cohen et al. ............. 623/17.15 |
| 6,468,543 | B1 | 10/2002 | Gilbertson et al. |
| 6,527,773 | B1 | 3/2003 | Lin et al. |
| 6,530,955 | B2 | 3/2003 | Boyle et al. |
| 6,547,823 | B2 * | 4/2003 | Scarborough et al. .... 623/17.16 |
| 6,569,168 | B2 | 5/2003 | Lin |
| 6,579,321 | B1 * | 6/2003 | Gordon et al. ........... 623/17.16 |
| 6,638,310 | B2 | 10/2003 | Lin et al. |
| 6,696,073 | B2 | 2/2004 | Boyce et al. |
| 6,733,504 | B2 | 5/2004 | Lin et al. |
| 6,855,167 | B2 | 2/2005 | Shimp et al. |
| 6,863,694 | B1 | 3/2005 | Boyce et al. |
| 6,911,045 | B2 | 6/2005 | Shimp |
| 2001/0020186 | A1 | 9/2001 | Boyce et al. |
| 2001/0043258 | A1 | 11/2001 | Ohki |
| 2002/0029084 | A1 * | 3/2002 | Paul et al. ................ 623/23.63 |
| 2002/0045897 | A1 | 4/2002 | Dixon et al. |
| 2002/0058950 | A1 | 5/2002 | Winterbottom et al. |
| 2002/0128717 | A1 | 9/2002 | Alfaro et al. |
| 2002/0161445 | A1 | 10/2002 | Crozel |
| 2002/0188295 | A1 | 12/2002 | Martz et al. |

OTHER PUBLICATIONS

Albee, Fred H., "Bone Surgery with Machine Tools," *Scientific American*, Apr. 1936, pp. 178-181.

*Allograft Freeze-Dried Release Specifications*, Osteotech, Inc., Sep. 30, 1992, 3 pages.

Brantigan, J.W., DePuy AcroMed, Lumbar I/F Cage With VSP Spinal System (Surgical Technique) (1999).

Crowe et al., "Inhibition of Enzymatic Digestion of Amylose by Free Fatty Acids in Vitro Contributes to Resistant Starch Formation", J. Nutr. 130(8): 2006-2008, 2000.

DePuy AcroMed, Lumbar I/F Cage Implants & Instruments (Product Catalog) (1999).

Driessens et al., "Calcium phosphate bone cements," *Universitat Politecnica de Catalunya*, Barcelona, Spain, 31: 855-77.

Edwards et al., "Osteoinduction of Human Demineralized Bone: Characterization in Rat Model", Clinical Orthopaedics and Related Research, No. 357, pp. 219-228 (1998).

Frymoyer et al., Eds., "The Adult Spine Principles and Practice," *Poster Lumbar Interbody Fusion*, James W. Simmons, vol. 2, pp. 1961-1987 (1991).

Gerhart et al. "Biomechanical optimization of a model particulate composite for orthopaedic applications," *J. Orthop. Res* (1986); 4(1): 86-85 [abstract only].

Glowacki et al., "Fate of Mineralized and Demineralized Osseous Implants in Cranial Defects", Calcified Tissue Int. 33: 71-76, 1981.

Glowacki et al., "Demineralized Bone Implants", Symposium on Horizons in Plastic Surgery, vol. 12, No. 2, pp. 233-241 (1985).

Han et al. "Quantitative and sensitive in vitro assay for osteoinductive activity of demineralized bone matrix," J. Orthop. Res., 21(4): 648-54, 2003.

Jain et al., "Anchoring of phospholipase A2: the effect of anions and deuterated water, and the role of N-terminus region," *Biochem. et Biophys. Acta*, 860:448-61, 1986.

Katz, "The biology of heavy water," *Scientific American*, 106-116, 1960.

Lewandrowski et al., "Improved Osteoinduction of Cortical Bone Allografts: A Study of the Effects of Laser Perforation and Partial Demineralization," *J. Ortho Res*. 15:748-756 (1997).

Ma, G.W.C., Posterior Lumbar Interbody Fusion with Specialized Instruments, *Clinical Ortho and Rel. Res.*, 193 (Mar.) pp. 57-63 (1985).

McCord et al., "Anterior endoscopic thoracolumbar instrumentation and implants," *Curr. Ortho 12*, pp. 96-103 (1998).

MTF Bone Catalog, Fibular Wedges, Femoral Struts, Tibial Struts, published prior to 2000, 1 page.

Neigal et al., "Use of Demineralized Bone Implants in Orbital and Craniofacial", Opthal. Plast. Reconstrs. Surg., 12: 108-120, 1996.

Ray et al., "Preliminary Report of an Experimental Study", J. Bone Joint Surgery, 39 A: 1119-1128, 1957.

Russell et al., "Clinical Utility of Demineralized Bone Matrix for Osseous Defects, Arthrodesis and Reconstruction: Impact of Processing Techniques and Study Methodology", Orthpaedics, 22(5): 524-531, 1999.

Smith, MD et al. "Load-bearing capacity of corticocancellous bone grafts in the spine" (truncated abstract), Aug. 1993, *Journal of Bone & Joint Surgery*, 75(8): 1206-13.

Sofamar Danek, "Surgical Technique Using Bone Dowel Instrumentation for Anterior Approach" [Publication Date Unknown].

Stevenson, S., "Enhancement of Fracture Healing with Autogenous and Allogenic Bone Grafts," *Clin. Ortho, Rel. Res*. 355S, pp. S239-S246 (1998).

Tan et al., A modified technique of anterior Lumbar fusion with femoral cortical allograft; *J. Orthop. Surg. Tech*; vol. 5, No. 3 91990), pp. 83-93.

Ueland et al., "Increased Cortical Bone Content of Insulin-Like Growth Factors in Acromegalic Patients", J. Clin. Endocrinol. Metab., 84(1): 123-127, 1999.

University of Florida Tissue Bank, Inc., Allograft Catalog [Publication Date Unknown].

University of Florida Tissue Transplant Patient Education Series [Publication Data Unknown].

Urist et al., "Observations implicating an extracellular enzymic mechanism of control of bone morphogenesis," *J. Histochem & Cytochem*, 22(2): 88-103, 1974.

Urist et al., "Preservation and biodegradation of the morphogenetic property of bone matrix," *J. Theor. Biol*. 38: 155-67, 1973.

Urist, "Bone: Formation by Autoinduction", Science, 150: 893-899, 1965.

VG2 Interbody Bone Grafts, DuPuy AcroMed, 2000, 6 pages.

Vich, Jose M. Otero, "Anterior cervical interbody fusion with threaded cylindrical bone," J. Neurosurg. 63:750-753, 1985.

Whiteman et al., "Demineralized Bone Powder—Clinical Applications for Bone Defects of the Hand", J. Hand. Surg., 18B: 487-490, 1993.

Whittaker et al., "Matrix Metalloproteinases and Their Inhibitors—Current Status and Future Challenges", Celltransmissions, 17(1): 3-14.

Xiabo et al., "Experimental and Clinical Investigations of Human Insoluble Bone Matrix Gelatin", Clin. Orthrop. 293: 360-365, 1993.

Zhang et al., "A Quantitative Assessment of Osteoinductivity of Human Demineralized Bone Matrix", J. Periodontol. 68(11): 1076-1084, 1997.

\* cited by examiner

US 7,662,185 B2

INTERVERTEBRAL IMPLANTS

This application claims priority as a divisional application from and incorporates by reference U.S. Utility application Ser. No. 09/754,038, filed Jan. 2, 2001, now abandoned, which claims priority from U.S. Provisional Application Ser. No. 60/173,973, filed Dec. 30, 1999.

BACKGROUND

1. Technical Field

The present disclosure relates generally to biocompatible implants and, more particularly, to intervertebral implants suitable for implantation into the lumbar, thoracic and/or cervical regions of the spine during a spinal fusion procedure.

2. Background of Related Art

Intervertebral implants for fusing together adjacent vertebrae of a spinal column are well known in the art. Such implants are formed in a variety of different shapes and sizes and are configured for insertion into receiving beds formed in the lumbar, thoracic and cervical regions of the spine. The implants may be formed from a variety of different biologically compatible materials including ceramics, polymers, human or animal bone, composites, etc. The implants may also be shaped to maintain the natural lordoses of the spine or to prevent the implant from backing out of an intervertebral receiving bed in which it will be implanted.

Examples of known implants are disclosed in U.S. Pat. No. 4,877,020 to Vich and U.S. Pat. No. 4,878,915 to Brantigan. Vich and Brantigan each disclose cylindrical implants having an outer helical thread formed thereabout. The Vich implant is formed from autogenic bone taken from the iliac crest of a patient. The Brantigan implant is formed of an inert metal such as stainless steel, cobalt-chromium-molybdenum alloys and titanium.

One problem associated with known implants is the difficulty in adapting an implant to meet the size requirements of a particular intervertebral receiving bed. For example, because anatomically all patients are different, the specific size of implant required for a surgical procedure will not be known to any certainty until a surgeon has prepared the intervertebral space for implantation. Thus, a surgeon must keep a variety of different size implants available for use or have means to alter the dimensions of the implant at his disposal.

Another problem associated with known implants constricted from bone is that the anatomical limitations of donor bone limit the size of the implant which can be formed from bone. As a result, bone having satisfactory strength characteristics may not be available for use as an implant because of size limitations.

Finally, yet another problem associated with known implants is their inability to accurately maintain the natural lordoses of the spine. Because of the irregular shape of the vertebral endplates, wedge-shaped implants and cylindrical dowels are incapable of supporting adjacent vertebrae in their natural orientation without substantially altering the shape of the vertebral endplate(s).

Accordingly, a continuing need exists for an intervertebral implant whose size may be easily altered by a surgeon during a surgical procedure to meet the size requirements of a particular implant receiving bed and for an implant capable of maintaining the natural lordoses of the spine without substantially altering the shape of the vertebral endplates.

SUMMARY

In accordance with the present disclosure, intervertebral implants are provided which more precisely correspond in shape to the shape of the vertebral endplates. In one preferred embodiment, an implant is formed from a ring of material having a top surface and a bottom surface. The top and/or bottom surfaces of the implant include a series of annular stepped surfaces which together define a convex configuration which closely corresponds to the concave shape of the vertebral endplates. In an alternate embodiment, the annular stepped surfaces on the top and/or bottom surfaces of the implant can be replaced by a single helical pathway.

In another preferred embodiment, a multipart intervertebral implant is provided which includes an implant portion and an implant extender portion. The implant portion and the implant extender portion can be fastened together using any known fastening means including pins, interlocking structure (e.g., dovetail, tongue and groove, etc.), adhesives, etc. The size of the implant extender portion can be selected during a surgical procedure to provide an implant suitable for a particular intervertebral receiving bed.

In yet another preferred embodiment, an intervertebral implant may be formed from a multiplicity of implant sections which are fastened together to provide an implant having a desired length. These implant sections and the implants described above can be formed of any biocompatible material including bone.

BRIEF DESCRIPTION OF THE DRAWINGS

Preferred embodiments of the presently disclosed intervertebral implants are described herein with reference to the drawings, wherein.

DETAILED DESCRIPTION OF PREFERRED EMBODIMENTS

Figure 1:
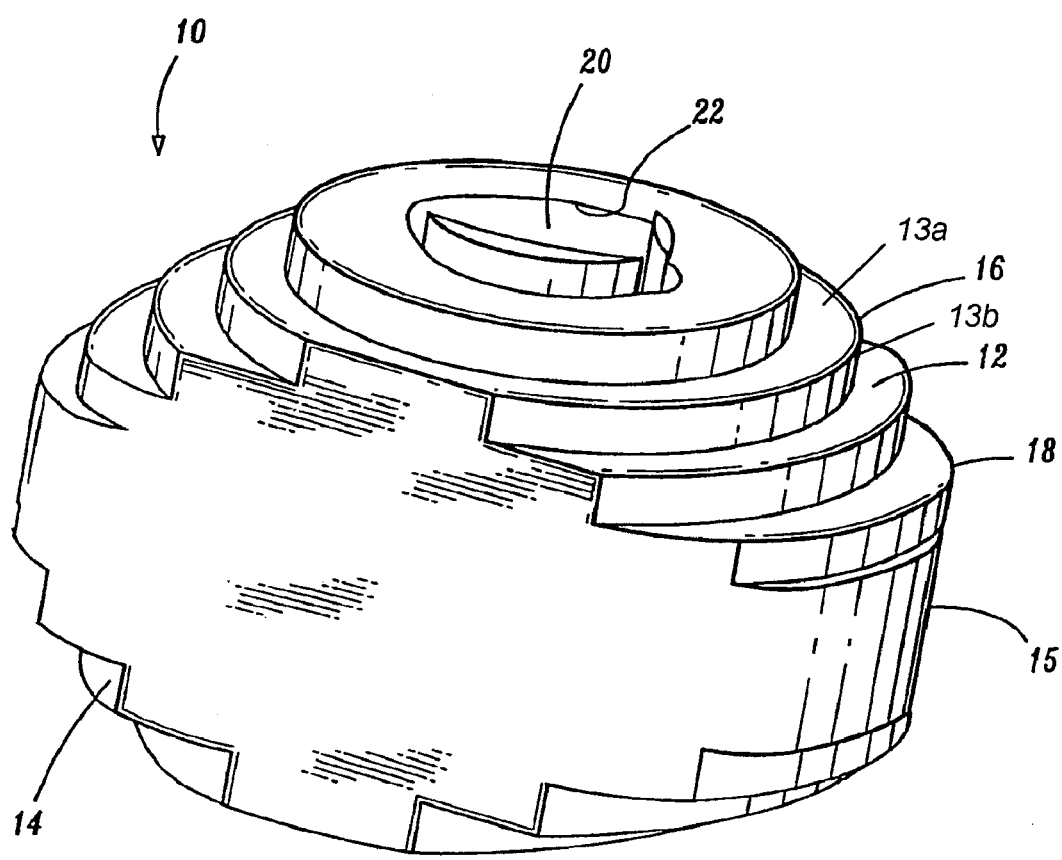
FIG. 1 is a perspective view of one preferred embodiment of the presently disclosed intervertebral implant.
Figure 2:
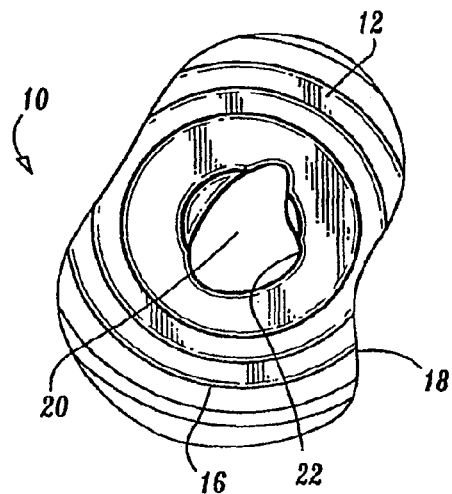
FIG. 2 is a top view of the intervertebral implant shown in FIG. 1.
Figure 3:
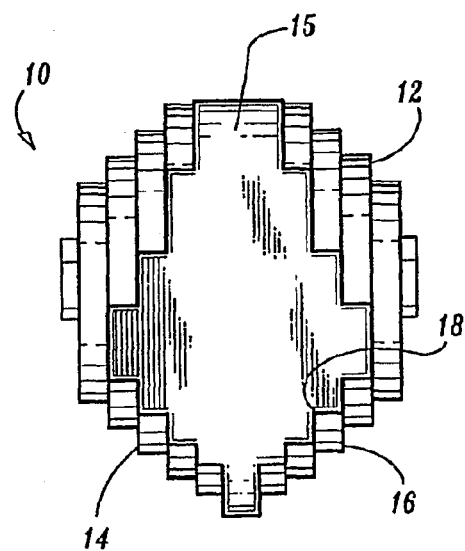
FIG. 3 is a side view from a first side of the intervertebral implant shown in FIG. 1.
Figure 4:
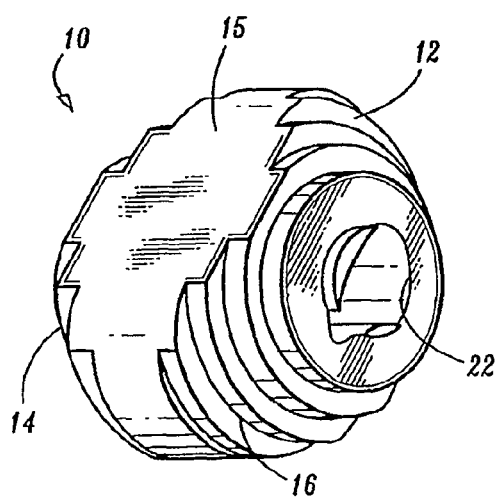
FIG. 4 is a top perspective view of the intervertebral implant shown in FIG. 1.
Figure 5:
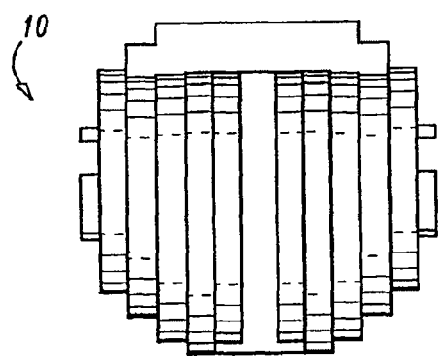
FIG. 5 is a side view from the other side of the intervertebral implant shown in FIG. 1.

Preferred embodiments of the presently disclosed intervertebral implant and implant extender will now be described in detail with reference to the drawings in which like reference numerals designate identical or corresponding elements in each of the several views.

FIGS. 1-5 illustrate a preferred embodiment of the presently disclosed intervertebral implant shown generally as 10. Briefly, implant 10 includes an upper surface 12, a lower surface 14 and a sidewall 15 positioned between the upper and lower surfaces. Upper and lower surfaces 12 and 14 each include a series of circular steps 16 which move upwardly from the outer periphery 18 of implant 10 to the center 20 of implant 10. The steps 16 include a first plane 13a and a second plane 13b. The first plane 13a is defined by the crest portion of the curvilinear projection or step 16. As shown, the plane 13a may be generally flat. In some embodiments, the first plane 13a and second plane 13b may make a tapered configuration. In some embodiments, steps 16 may not be centered about the center of implant 10 and adjacent steps may not be of the same height. A throughbore 22 extends between upper and lower surfaces 12 and 14 of implant 10. Throughbore 22 is dimensioned to receive growth factors including autograft, allograft, DBM, etc. . . . , to stimulate bone growth. In some embodiments, at least a portion of the sidewall 15 is free of slits and extends continuously generally parallel relative to a longitudinal axis extending between the upper surface 12 and the lower surface 14 of the implant 10.

FIGS. 6-10 also illustrate an implant 100 having stepped upper and lower surfaces 112 and 114. In contrast to the implant shown in FIGS. 1-5, implant 100 includes a greater number of steps 116 which define a more gradual taper than steps 16 of implant 10. As shown, the implant may include an axis A extending between an upper and lower surface of the implant, wherein the curvilinear stepped surfaces 116 include a surface that is generally perpendicular to the axis A. It is to be appreciated that such axis A may be included in any of the embodiments disclosed herein, including, for example, the embodiment of FIGS. 1-5. It is envisioned that any number of steps may be provided on the upper and/or lower surfaces of the implant to provide any desired surface curvature. For example, each stop may have a height of from about 0.15 mm to about 3 mm. Other step dimensions are also envisioned. The implant 100 comprises a body 121 and includes a sidewall 119. As shown, the body 121 is substantially solid and the sidewall 119 is substantially continuous.

Figure 6:
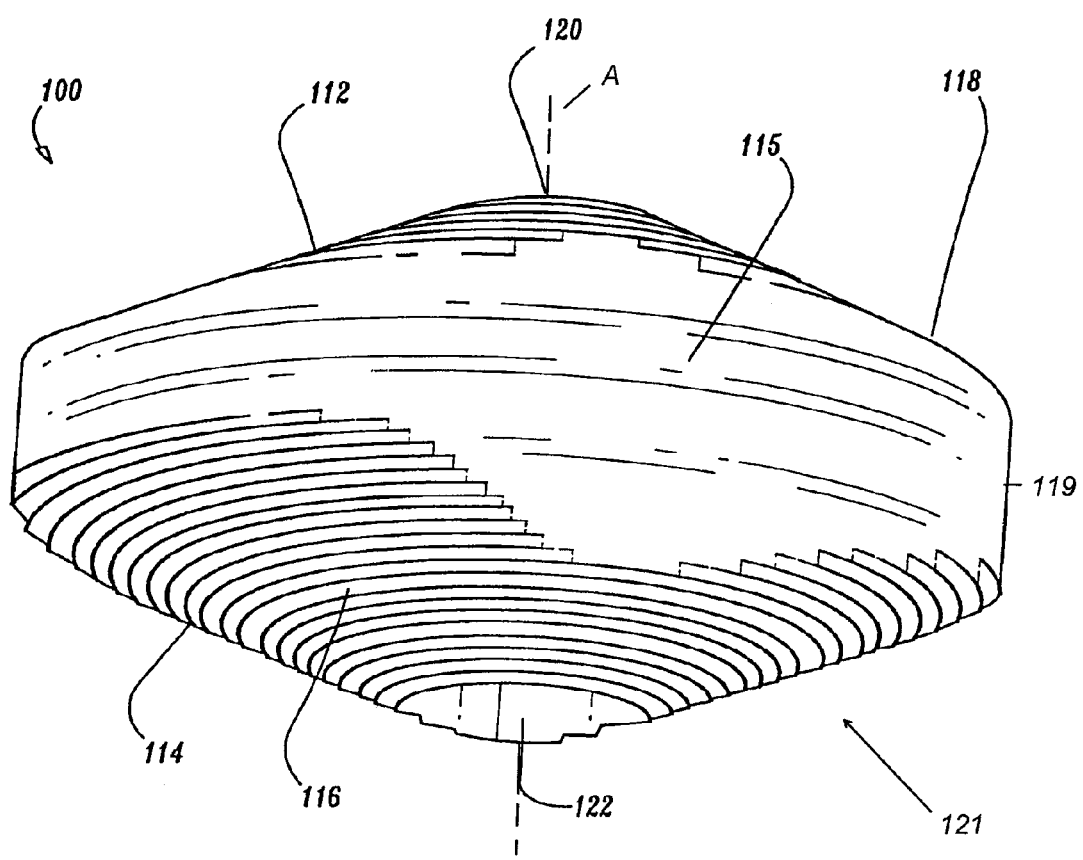
FIG. 6 is a perspective view of another preferred embodiment of the presently disclosed intervertebral implant.
Figure 6A:
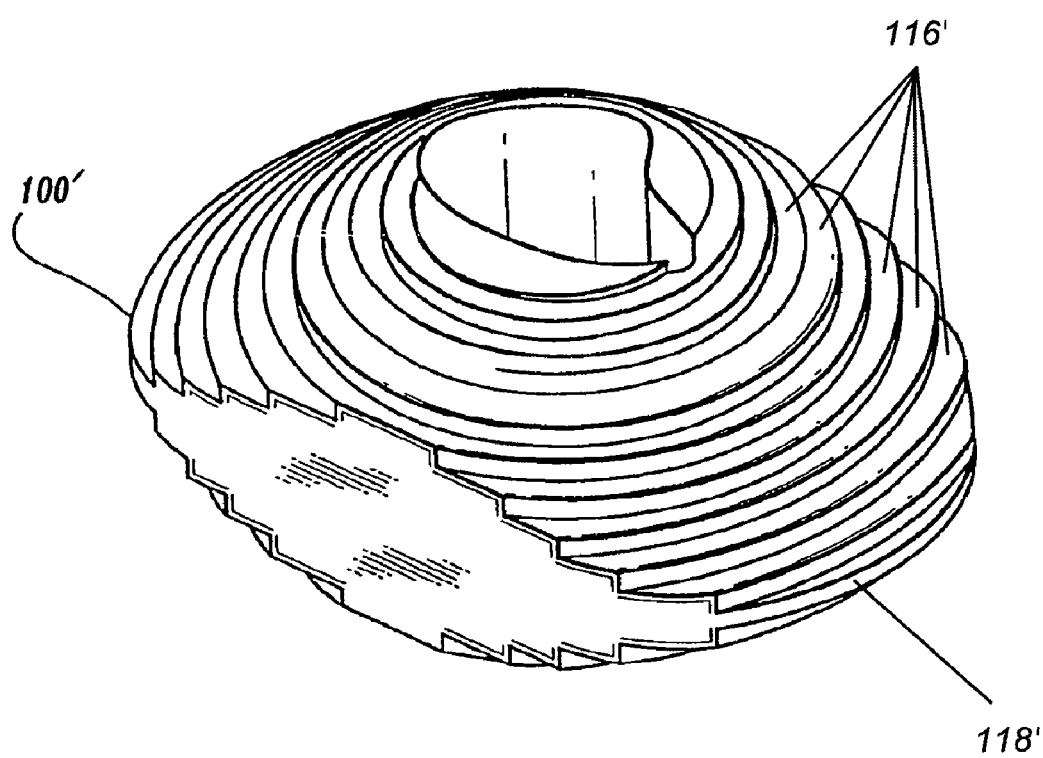
FIG. 6A is a perspective view of another preferred embodiment of the presently disclosed intervertebral implant.
Figure 7:
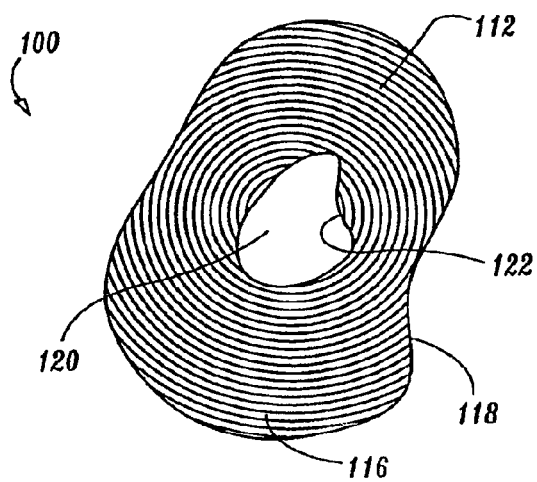
FIG. 7 is a top view of the intervertebral implant shown in FIG. 6.
Figure 8:
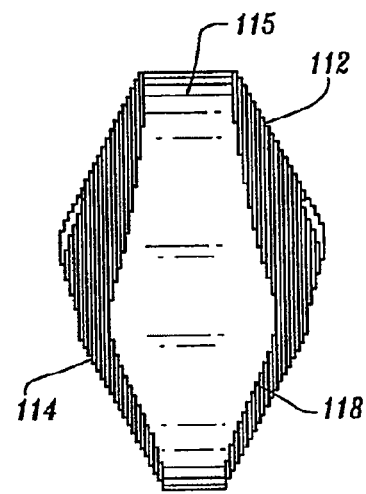
FIG. 8 is a side view of the intervertebral implant shown in FIG. 6.
Figure 9:
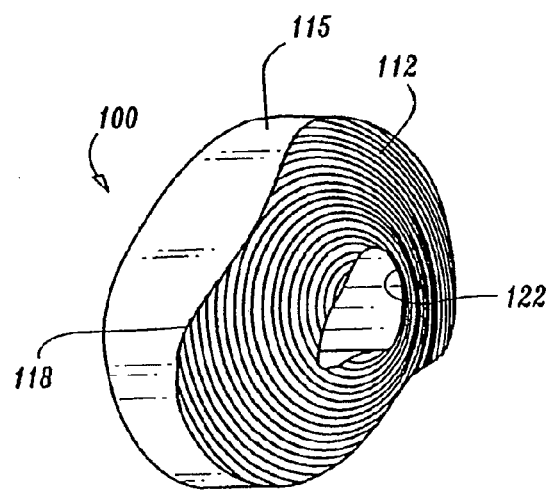
FIG. 9 is a top perspective view of the intervertebral implant shown in FIG. 6.
Figure 10:
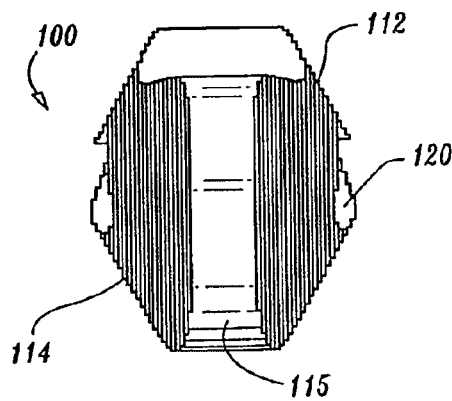
FIG. 10 is another side view of the intervertebral implant shown in FIG. 6.

FIG. 6A illustrates another alternate embodiment of the stepped implant shown in FIGS. 1-5 shown generally as 100'. Implant 100' includes a helical pathway 116' which extends from the outer periphery 118' of implant 100' towards the center of implant 100'. As discussed above, the helical pathway need not be centered about the central axis of implant 100' but rather it may be oriented to provide the desired curvature on the upper and/or lower surface of implant 100'. Moreover, the height of the step defined by the helical pathway 116' may vary along the length of pathway 116'.

Implants 10, 100 and 100' may be formed from a variety of different biologically compatible materials including ceramics, polymers, human or animal bone, carbon fiber tantalum composites, etc. using a variety of known processes including molding, casting, machining, etc. Preferably, implant 10 is formed from cadaveric human or animal bone by making a transverse cut through the diaphysis or metaphysis of a long bone, e.g., tibia, fibula, femur, ulna, radius, etc., to form a ring and thereafter machining the upper and/or lower surfaces of the implant, e.g., milling the stepped or helical configuration into the upper and lower surfaces of the ring. Alternately, only one of the upper and lower surfaces of the ring may be provided with a stepped configuration.

The bone used to form implants 10, 100 and 100' may be partially or fully demineralized bone. Preferably the bone is surface demineralized. By surface demineralizing the bone, the osteoconductivity and the conformability of the outer surfaces of the implant are improved while the strength of the inner portion of the implant is retained.

Figure 11:
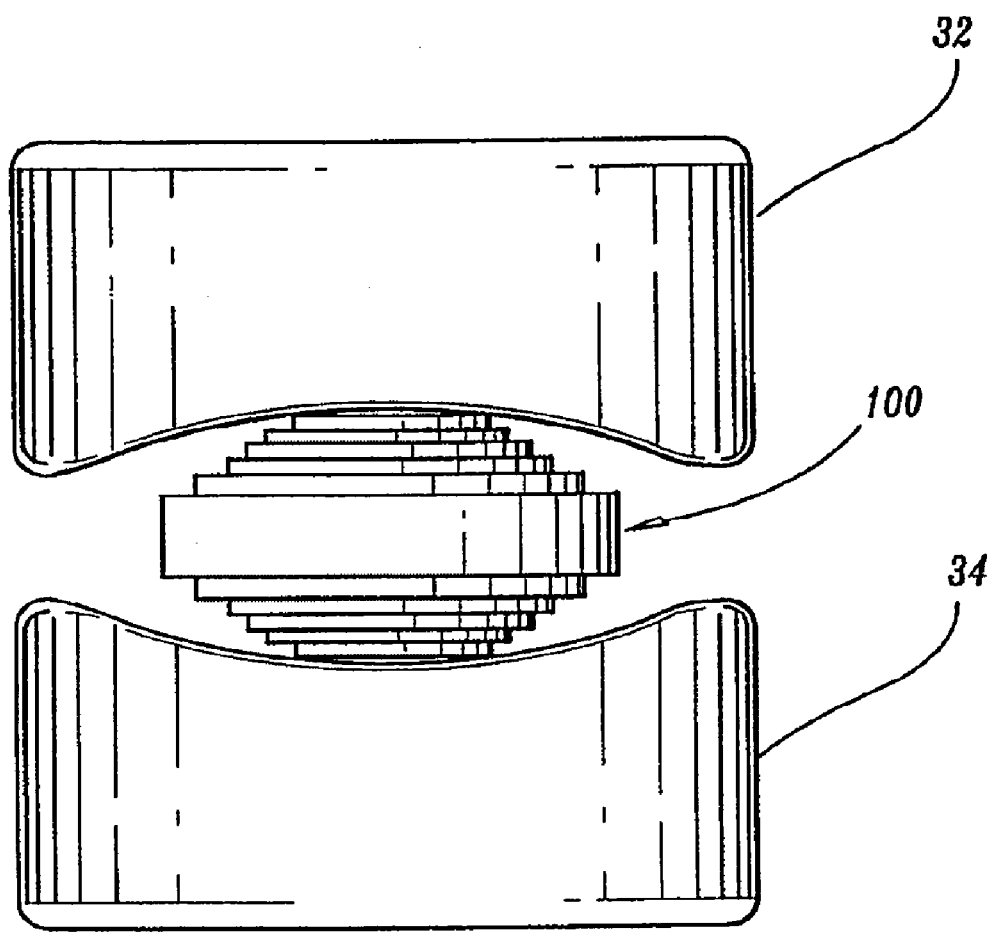
FIG. 11 is an elevational view of the intervertebral implant shown in FIG. 6 positioned between adjacent vertebrae.
Figure 13:
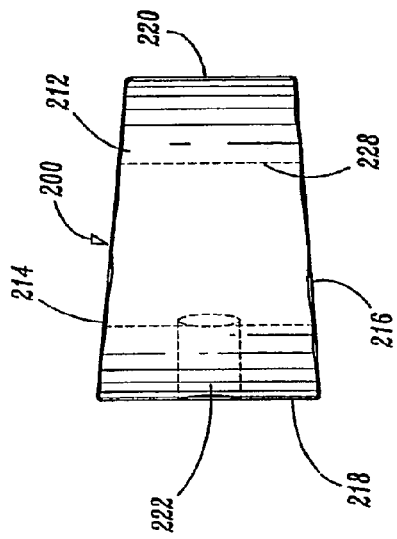
FIG. 13 is a side view of the intervertebral implant shown in FIG. 12.
Figure 15:
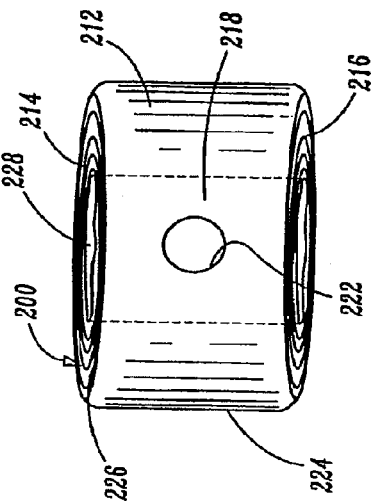
FIG. 15 is a rear end view of the intervertebral implant shown in FIG. 12.
Figure 12:
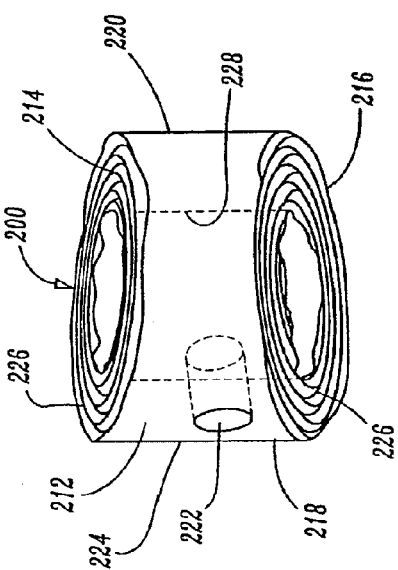
FIG. 12 is a perspective view of another embodiment of the presently disclosed intervertebral implant.
Figure 14:
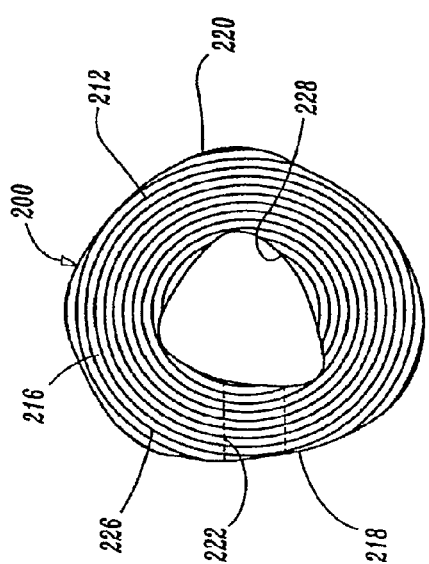
FIG. 14 is a top view of the intervertebral implant shown in FIG. 12.
Figure 17:
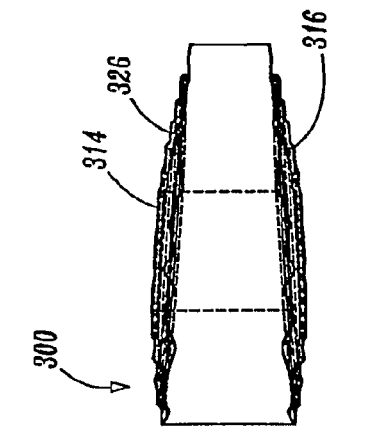
FIG. 17 is a side view of the intervertebral implant shown in FIG. 16.
Figure 19:
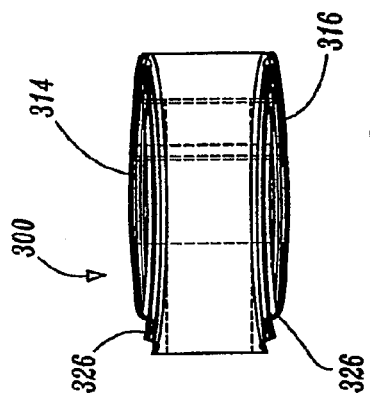
FIG. 19 is a rear end view of the intervertebral implant shown in FIG. 16.
Figure 16:
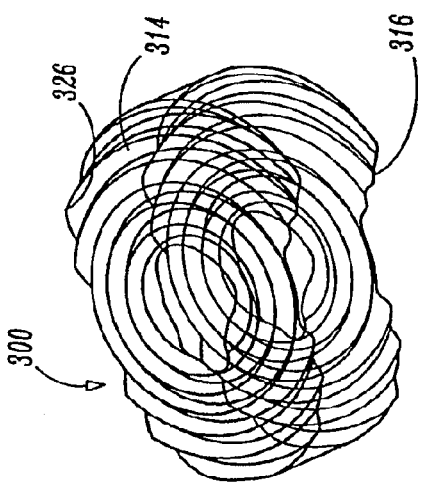
FIG. 16 is a perspective view of yet another embodiment of the presently disclosed intervertebral implant.
Figure 18:
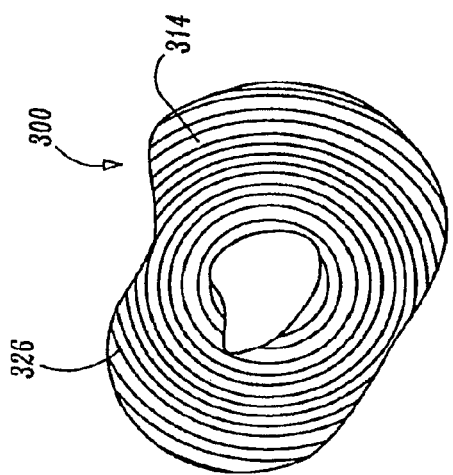
FIG. 18 is a top view of the intervertebral implant shown in FIG. 16.
Figure 21:
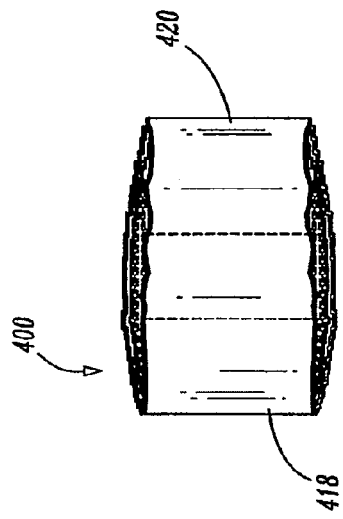
FIG. 21 is a side view of the intervertebral implant shown in FIG. 20.
Figure 23:
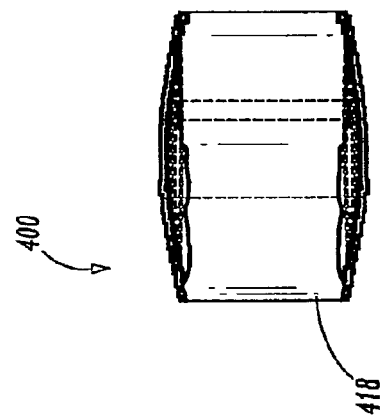
FIG. 23 is a rear end view of the intervertebral implant shown in FIG. 20.
Figure 20:
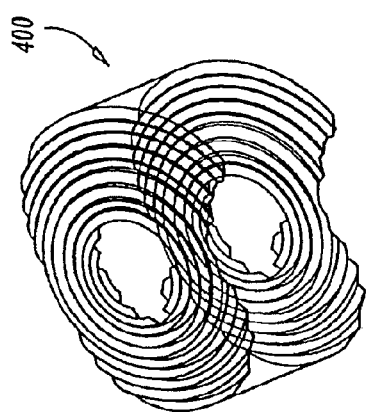
FIG. 20 is a perspective view of yet another embodiment of the presently disclosed intervertebral implant.
Figure 22:
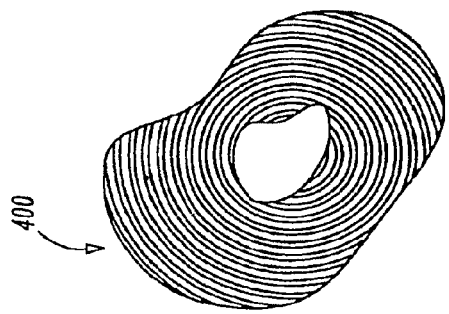
FIG. 22 is a top view of the intervertebral implant shown in FIG. 20.

Referring to FIG. 11, implants 10, 100 and 100' may be positioned within a receiving bed formed between adjacent vertebrae 32 and 34. Because the upper and lower surfaces of the implants conform to the natural concavity of the vertebral endplates, only minimal preparation of the vertebrae is required by a surgeon prior to insertion of an implant to maintain the natural lordoses of the spine.

FIGS. 12-15 illustrate an alternate embodiment of the intervertebral implant shown generally as 200. Intervertebral implant 200 is preferably formed from a cortical ring allograft cut from the diaphysis or metaphysis of a long bone but may be formed from any biocompatible material having the requisite strength requirements. Implant 200 includes a tapered, ring-shaped body 212 having flat top and bottom surfaces 214 and 216, respectively. Anterior end 218 of implant 200 has a height which is greater than the height of posterior end 220. The taper of the implant should be such as to conform to the vertebral end plates of adjacent vertebrae. Mating structure 222 for engaging corresponding structure of an insertion tool is formed in a sidewall 224 of implant 200 in the anterior end 218 of implant 200. A plurality of concentric rings 226 are formed in top and bottom surfaces 214 and 216. Rings 226 are preferably V-shaped, although other configurations are also envisioned, i.e., U-shaped, rectangular, etc. A throughbore 228 extends between top and bottom surfaces 214 and 216 of implant 200. If implant 200 is formed from bone, throughbore 228 may be defined by the intramedullary canal of the bone from which implant 200 is cut. Implant 200 is configured for anterior insertion into the intervertebral space. Growth factors including autograft, allograft, and demineralized bone particles may be positioned in throughbore 228 and/or rings 226 to stimulate bone growth.

FIGS. 16-19 illustrate an alternate embodiment of implant 200 shown generally as 300. Implant 300 is similar to implant 200 but includes convex top and bottom surfaces 314 and 316 which are configured to engage the vertebral end plates of adjacent vertebrae. Top and bottom surfaces 314 and 316 also include concentric rings 326 similar to those described above with respect to implant 200.

FIGS. 20-23 illustrate another alternate embodiment of implant 200 shown generally as 400. Implant 400 is similar to implant 200 except that anterior end 418 is approximately equal to the height of posterior end 420.

Figure 24:
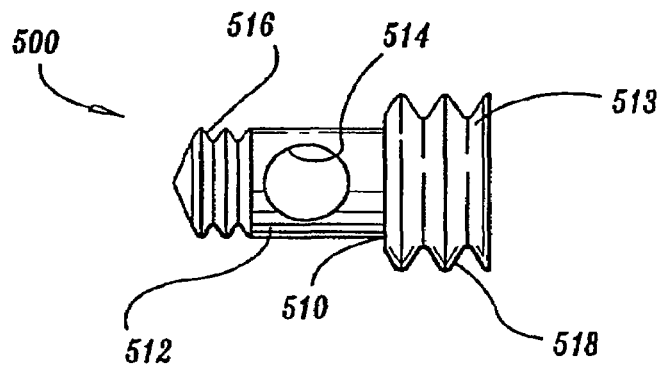
FIG. 24 is a top view of yet another embodiment of the presently disclosed intervertebral implant.

FIG. 24 illustrates a partially threaded stepped implant shown generally as 500. Implant 500 is preferably formed from cortical bone by making a transverse cut through the diaphysis or metaphysis of a long bone to obtain a cylindrical bone plug and thereafter machining and threading the bone plug. Alternately, implant 500 may be formed from any biocompatible material having the requisite strength requirements using any known process including machining, molding, etc. Implant 500 includes a cylindrical body 510 having a first end portion 512 having a first outer diameter and a second end portion 513 having a second outer diameter larger than the first diameter. A variety of different diameter implants are envisioned. A throughbore 514 extends through first end portion 512 of cylindrical body 510. First end portion 512 has screw threads 516 at one end thereof, but does not include threads in the area about throughbore 514. Second end portion 513 includes screw threads 518. When implant 500 is formed by cutting a bone plug from a long bone, the absence of screw threads in the area of throughbore 514 facilitates the use of long bones having a thinner wall section, i.e., the bone wall between the intramedullary canal of a long bone and the outer surface of the bone plug cut therefrom can be thinner.

When implant 500 is inserted into intervertebral space between adjacent vertebrae, second end portion 513 will sit in the vertebral wall and provide the majority of the retaining force. First end portion 512 will also screw into adjacent endplates but thread engagement may be minimal, especially if the intervertebral space is very concave. A stepped reamer and tap can be used to prepare the intervertebral space.

Figure 25:
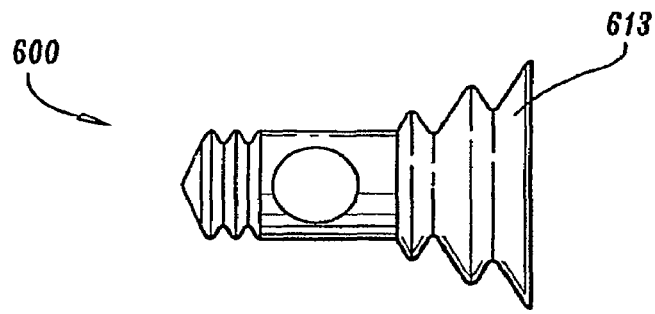
FIG. 25 is yet another embodiment of the presently disclosed intervertebral implant.
Figure 26:
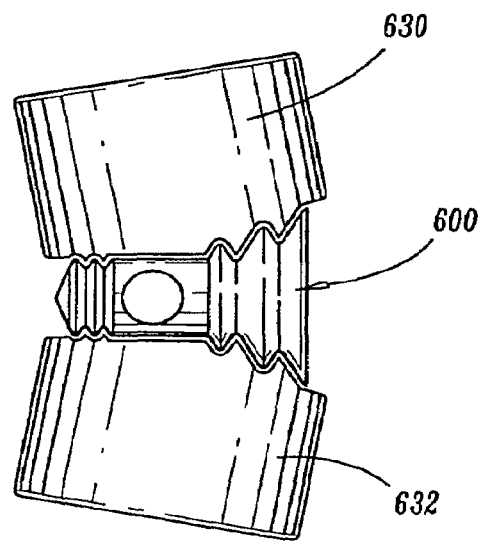
FIG. 26 is a side view of the intervertebral implant shown in FIG. 25 positioned between adjacent vertebrae.

FIGS. 25 and 26 illustrate an alternate embodiment of implant 500 shown generally as 600. Implant 600 is similar to implant 500 except that second end 613 of implant 600 is tapered from one end to the other. Implant 600 may be used to vary the spine geometry. Referring to FIG. 26, during insertion of implant 600 into the intervertebral space, implant 600 will directly force adjacent vertebral surfaces 630 and 632 apart. The particular taper of second end portion 613 of implant 600 can be chosen to provide the desired spacing of the adjacent vertebrae.

Intervertebral implants in the form of threaded, cylindrical dowels formed of bone, specifically, human or animal cadaveric bone, are well known in the surgical arts. Typically, such implants are formed by making a transverse cut through the diaphysis or metaphysis of a long bone, i.e., the femur, tibia, fibula, ulna or radius, using a cylindrical drill bit. One problem associated with forming and using bone dowel implants is that anatomical limitations make it difficult to recover bone dowels having the desired length needed for intervertebral fusion procedures. This is especially true when performing procedures in the cervical region of the spine wherein small diameter dowels are required.

Figure 27:
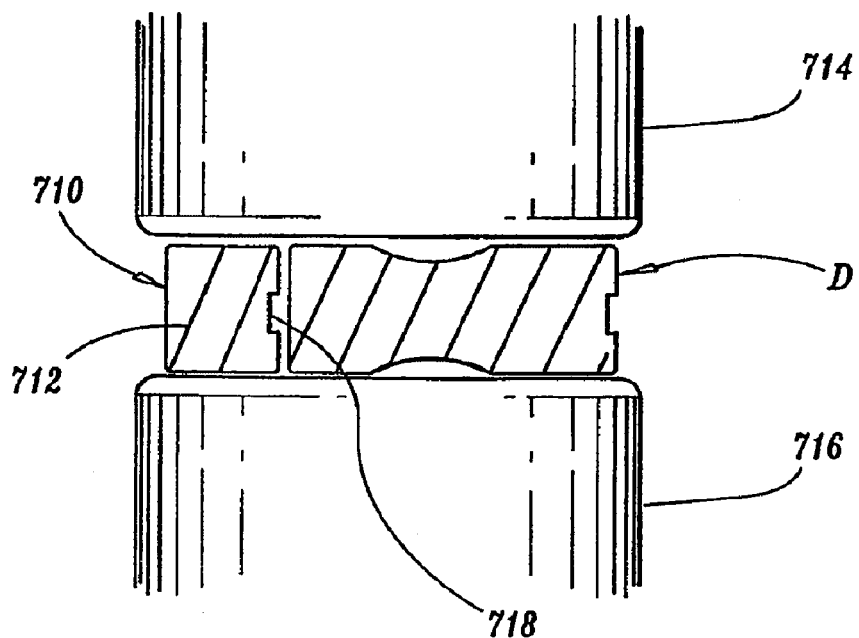
FIG. 27 is a side view of the presently disclosed intervertebral implant and implant extender positioned between adjacent vertebrae with the implant extender positioned adjacent the leading end of the intervertebral implant.
Figure 28:
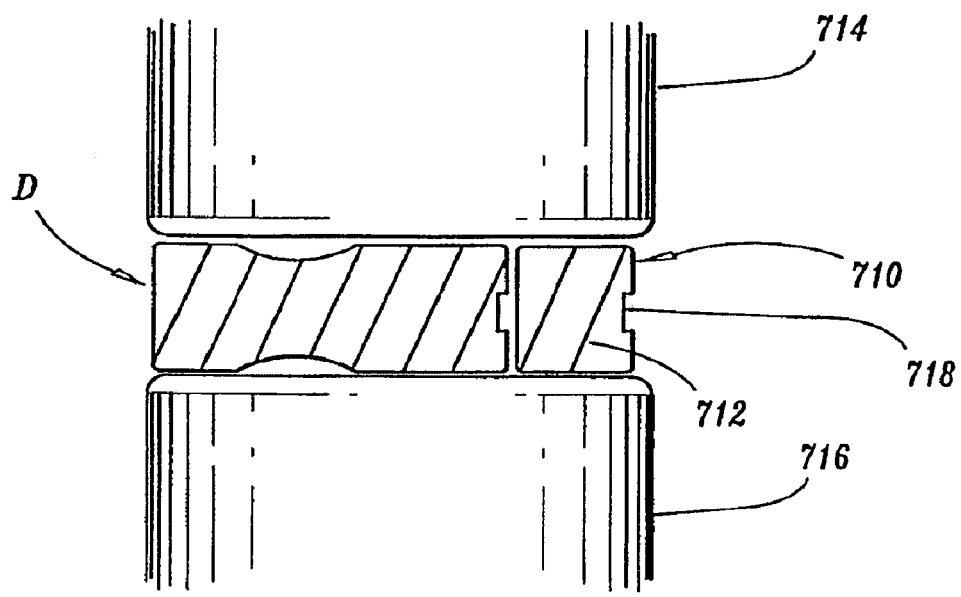
FIG. 28 is a side view of the intervertebral implant and implant extender shown in FIG. 27 positioned between adjacent vertebrae with the implant extender positioned adjacent the trailing end of the intervertebral implant.

In order to compensate for anatomical limitations, a dowel extender portion may be provided. Referring to FIGS. 27 and 28, a cylindrical dowel extender 710 may be implanted within the intervertebral space prior to implantation of the main dowel portion D (FIG. 27), or alternately, after implantation of main dowel portion D (FIG. 28). Preferably, dowel extender portion 710 includes helical threads 712 to engage vertebral end plates 714 and 716 and retain the dowel extender portion in place. However, non-threaded dowel extender portions are also envisioned. Each dowel extender portion 710 preferably includes engagement structure, such as slot 718, for engaging an insertion tool (not shown).

Generally, dowel extenders having a length of from about 4 to 8 mm are needed to supplement the main dowel, although other length dowel extenders may also be needed depending upon the particular surgical procedure being performed. A common thread pattern associated with intervertebral dowels is 10 threads per inch. Thus, a dowel extender having a length of 4 mm will only have about 1.57 threads and a dowel extender having a length of 6 mm will have only about 2.35 threads. Because of the limited number of threads and the short thread engagement length, it may be difficult to stabilize a dowel extender in the intervertebral space and problems may result. For example, if the dowel extender is not firmly seated in the intervertebral space between adjoining vertebrae when contacted by the main dowel, it may tip over.

Figure 29:
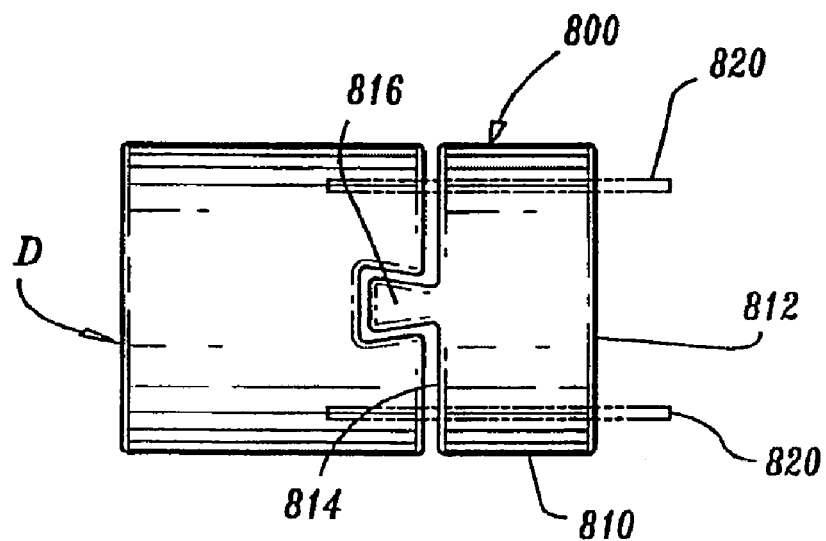
FIG. 29 is a side view of an alternate embodiment of the presently disclosed intervertebral implant and implant extender in an interlocked configuration.
Figure 30:
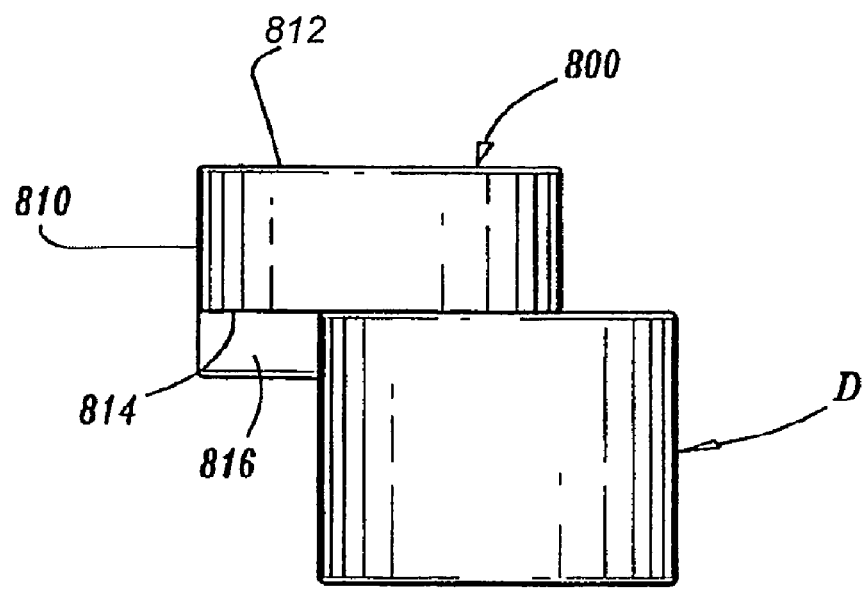
FIG. 30 is a side view of the intervertebral implant and implant extender shown in FIG. 29 in a partially assembled configuration.

In order to provide greater stability, an alternate embodiment of the presently disclosed dowel extender is described herein. Referring to FIGS. 29 and 30, dowel extender 800 includes a cylindrical body 810 having a first end 812 and a second end 814. Second end 814 includes a projection 816 configured and dimensioned to be received within a correspondingly shaped slot formed on one end of main dowel D. Although illustrated as having a dove-tail configuration, projection 816 may assume other configurations capable of interlocking with a correspondingly shaped slot. Referring to FIG. 29, locking pins 820 may be provided to further secure dowel extender portion 800 to main dowel portion D. Alternately, a locking pin or pins may be used to entirely replace projection 816 and secure dowel extender 800 to main dowel D.

In an alternate embodiment, a bone dowel is constructed from multiple dowel segments which are secured together using interlocking structure. The interlocking structure may be formed integrally with each dowel segment, e.g., each dowel segment may have a slotted front end and a correspondingly shaped projection formed at a rear end. Each dowel segment has a predetermined length and is joined to one or more other dowel segments to form a dowel having a desired length. For example, dowel segments may be formed having lengths of 2, 4 and 6 mm. In order to form a dowel having a length of 20 mm, three 6 mm dowel segments and a 2 mm dowel segment can be joined together. The dowel segments are preferably formed from bone, although other biocompatible materials listed above are also envisioned. The dowel segments may be cylindrical, rectangular, wedge-shaped, etc.

Figure 31:
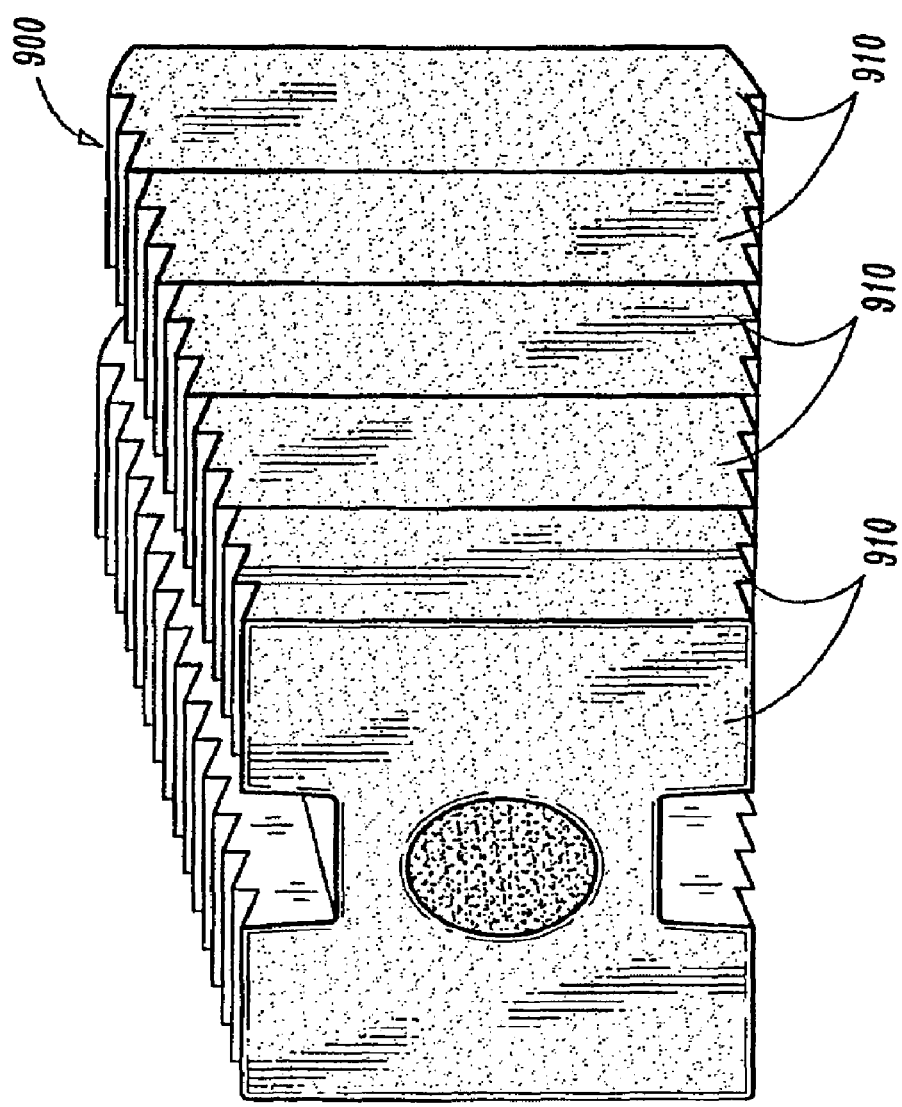
FIG. 31 is a perspective view of yet another embodiment of the presently disclosed intervertebral implant.

For example, FIG. 31 illustrates a wedge shaped intervertebral implant 900 formed of multiple implant segments 910 which are fastened together in the manner described above.

It will be understood that various modifications may be made to the embodiments disclosed herein. For example, the configuration of the sidewall of any of the implants described above may be modified to better suit a particular procedure, i.e., the sidewalls can be formed to be rectangular, circular, triangular, semi-circular, etc. Moreover, the implants described above, although disclosed in the context of spinal implantation, may be suitable for other implantation procedures not specifically listed here but obvious to those of ordinary skill in the art. Therefore, the above description should not be construed as limiting, but merely as exemplifications of preferred embodiments. Those skilled in the art will envision other modifications within the scope and spirit of the claims appended hereto.

The invention claimed is:

1. An intervertebral implant for implanting within an intervertebral space defined between adjacent vertebrae, the implant comprising:
    an upper region opposite a lower region, a side-wall, and a longitudinal axis extending between said upper and lower regions, each of the regions including a series of curvilinear stepped surfaces, wherein the curvilinear stepped surfaces comprise a surface that is generally perpendicular to the axis, the series of curvilinear stepped surfaces together defining a convex configuration in each of the upper region and the lower region; and
    at least a portion of the side-wall free of slits extending continuously generally parallel relative to the longitudinal axis from the upper region to the lower region.

2. The intervertebral implant according to claim 1 further including a throughbore extending between the upper and lower regions.

3. The intervertebral implant according to claim 1 wherein the series of curvilinear stepped surfaces are defined by a helical pathway.

4. The intervertebral implant according to claim 1 wherein the implant is formed from at least one material selected from the group consisting of bone, polymer, ceramic and carbon fiber.

5. An intervertebral implant for implanting within an intervertebral space, comprising:
    an upper region opposite a lower region, a side-wall, and a longitudinal axis extending between the upper and lower regions, the upper and lower regions including a plurality of stepped curvilinear projections formed thereon, wherein the curvilinear projections comprise a surface that is generally perpendicular to the axis;
    at least a portion of the side-wall free of slits extending continuously generally parallel relative to the longitudinal axis from the upper region to the lower region; and
    a throughbore extending between the upper and lower regions.

6. An intervertebral implant according to claim 5 wherein each plane defined by crest portions of the plurality of curvilinear projections of the upper and lower regions is generally flat.

7. The intervertebral implant according to claim 5, wherein two planes defined by crest portions of the plurality of curvilinear projections of the upper and lower regions make a tapered configuration.

8. The intervertebral implant according to claim 5, wherein the implant is formed from at least one material selected from the group consisting of bone, polymer, ceramic and carbon fiber.

9. The intervertebral implant according to claim 5, wherein the implant is formed from bone, and further wherein the throughbore is defined by an intramedullary canal formed in the bone.

10. A method for implantation of an intervertebral implant within an intervertebral space defined between adjacent vertebra, comprising the steps of:
    accessing an intervertebral space defined between adjacent vertebrae;
    preparing a receiving bed in the intervertebral space;
    providing an intervertebral implant, the implant including an upper region opposite a lower s region, a side-wall, and a longitudinal axis extending between the upper and lower regions, at least a portion of the side-wall free of slits extending continuously generally parallel relative to the longitudinal axis from the upper region to the lower region; and
    each region including a series of curvilinear stepped surfaces, the stepped curvilinear surfaces comprising a surface that is generally perpendicular to the axis, wherein the series of curvilinear stepped surfaces together define a convex configuration in each of the upper region and the lower region closely corresponding to a concave shape of vertebral endplates of the adjacent vertebrae ; and
    positioning the intervertebral implant within the receiving bed such that the convex configuration defined by the curvilinear stepped surfaces closely match to the concave vertebral endplates of the adjacent vertebrae.

11. An intervertebral implant for implanting within an intervertebral space defined between adjacent vertebrae, the implant comprising:
    an upper region opposite a lower region, a side-wall, and a longitudinal axis extending between the upper and lower regions, at least a portion of the side-wall free of slits extending continuously generally parallel relative to the longitudinal axis from the upper region to the lower region; and each of the regions including a series of curvilinear stepped surfaces, the curvilinear stepped surfaces each comprising a surface that is generally parallel to the axis, the series of curvilinear stepped surfaces together defining a convex configuration in each of the upper region and the lower region.

12. An intervertebral implant for implanting within an intervertebral space, comprising:
    an upper region opposite a lower region, a side-wall, and a longitudinal axis extending between the upper and lower regions, at least a portion of the side-wall free of slits extending continuously generally parallel relative to the longitudinal axis from the upper region to the lower region, the upper and lower regions including a plurality of stepped curvilinear projections formed thereon, the curvilinear projections each comprising a surface that is generally parallel to the axis; and
    a throughbore extending between the upper and lower surfaces regions.

13. A method for implantation of an intervertebral implant within an intervertebral space defined between adjacent vertebra, comprising the steps of:
    accessing an intervertebral space defined between adjacent vertebrae;
    preparing a receiving bed in the intervertebral space;
    providing an intervertebral implant, the implant including an upper region opposite a lower region, a side-wall, and a longitudinal axis extending between the upper and lower regions, at least a portion of the side-wall free of slits extending continuously generally parallel relative to the longitudinal axis from the upper region to the lower region; and each region including a series of curvilinear stepped surfaces, the stepped curvilinear surfaces each comprising a surface that is generally parallel to the axis, wherein the series of curvilinear stepped surfaces together define a convex configuration in each of the upper region and the lower region closely corresponding to a concave shape of vertebral endplates of the adjacent vertebrae; and positioning the intervertebral implant within the receiving bed such that the convex configuration defined by the curvilinear stepped surfaces closely match to the concave vertebral endplates of the adjacent vertebrae.

* * * * *

UNITED STATES PATENT AND TRADEMARK OFFICE
CERTIFICATE OF CORRECTION

PATENT NO. : 7,662,185 B2  Page 1 of 1
APPLICATION NO. : 10/651390
DATED : February 16, 2010
INVENTOR(S) : Arthur A. Alfaro et al.

It is certified that error appears in the above-identified patent and that said Letters Patent is hereby corrected as shown below:

On the Title Page

INVENTORS

| | Item (75) | Item (75) Should Read |
|---|---|---|
| | "Daniel E. Rosenthal, Millburn, NJ" | -- Daniel E. Rosenthal, Short Hills, NJ -- |

| Column | Line | | Should Read |
|---|---|---|---|
| 1 | 49-50 | "implants constricted from bone" | -- implants constructed from bone -- |

Signed and Sealed this

Sixth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,662,185 B2
APPLICATION NO. : 10/651390
DATED : February 16, 2010
INVENTOR(S) : Alfaro et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 993 days.

Signed and Sealed this

Thirtieth Day of November, 2010

David J. Kappos
*Director of the United States Patent and Trademark Office*